(12) United States Patent
Linemann et al.

(10) Patent No.: US 10,183,907 B2
(45) Date of Patent: Jan. 22, 2019

(54) PROCESS FOR THE SYNTHESIS OF ACRYLIC ACID OLIGOMERS

(71) Applicant: Arkema France, Colombes (FR)

(72) Inventors: Reinhard Linemann, Saarbucken Allemagne (DE); Benoit Riflade, Bazas (FR); Serge Tretjak, Roulhing (FR); Andre Levray, Porcelette (FR); Patrice Defer, Courcelles-Chaussy (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/762,582

(22) PCT Filed: Sep. 7, 2016

(86) PCT No.: PCT/FR2016/052221
§ 371 (c)(1),
(2) Date: Mar. 23, 2018

(87) PCT Pub. No.: WO2017/055698
PCT Pub. Date: Apr. 6, 2017

(65) Prior Publication Data
US 2018/0265447 A1    Sep. 20, 2018

(30) Foreign Application Priority Data

Oct. 2, 2015 (FR) ...................... 15 59390

(51) Int. Cl.
*C07C 67/04* (2006.01)
*C07C 67/54* (2006.01)

(52) U.S. Cl.
CPC .............. *C07C 67/04* (2013.01); *C07C 67/54* (2013.01)

(58) Field of Classification Search
CPC .......... C07C 67/04; C07C 69/73; C07C 67/54
See application file for complete search history.

(56) References Cited

U.S. PATENT DOCUMENTS 4,267,365 A     5/1981   Findeisen
4,359,564 A  *  11/1982  Merritt .................... C08F 20/28
                                                    526/260

* cited by examiner

*Primary Examiner* — Yevgeny Valenrod
*Assistant Examiner* — Blaine G Doletski
(74) *Attorney, Agent, or Firm* — Lynn B. Morreale

(57) ABSTRACT

A process for the synthesis of acrylic acid oligomer represented by formula (I):

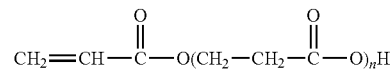

in which n is an integer ranging from 1 to 10, wherein the process comprises the step of heating acrylic acid at a temperature from 50° C. to 200° C. in the presence of a catalyst, water and at least one polymerization inhibitor. Formula (I) where n=0 is acrylic acid, the precursor for preparing the acrylic acid oligomer.

11 Claims, 1 Drawing Sheet

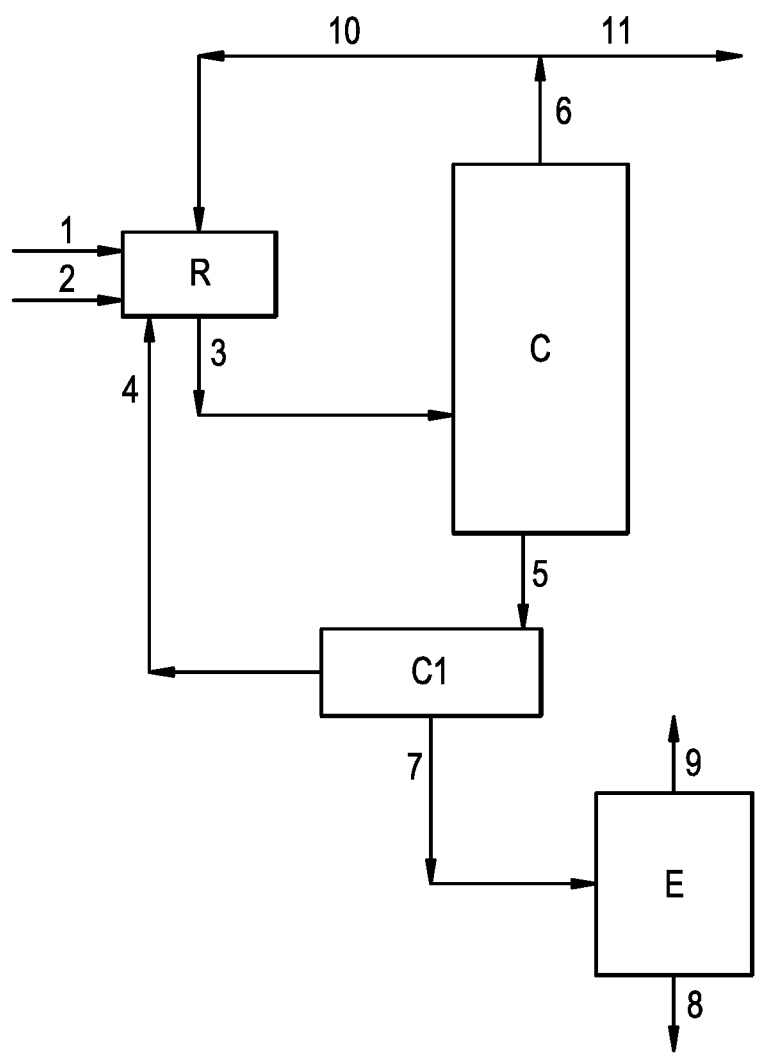

PROCESS FOR THE SYNTHESIS OF ACRYLIC ACID OLIGOMERS

CROSS-REFERENCE TO RELATED APPLICATIONS

This application is a national stage application under 35 U.S.C. § 371 of PCT/FR201.6/052221, filed Sep. 7, 2016 which claims benefit to application FR15.59390, filed Oct. 2, 2015.

TECHNICAL FIELD

The present invention relates to the synthesis of an acrylic monomer, in particular of an acrylic acid oligomer, represented by formula (I):

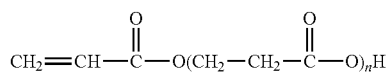

in which n is an integer ranging from 1 to 10, that can be used as a (co)monomer for producing acrylic polymers.

PRIOR ART

It is known from U.S. Pat. No. 4,267,365 to prepare acrylic acid oligomers corresponding to formula (I) in which n is between 1 and 6, preferably between 1 and 3, by heating acrylic acid at a temperature ranging from approximately 50° C. to 200° C. in the presence of a polymerization inhibitor at a content ranging from 0.001% to 1% by weight relative to the amount of acrylic acid. The process is carried out under a pressure of generally between 20 Torr and 50 atmospheres, optionally in the presence of an inert solvent. By adjusting the temperature and/or the residence time, it is possible to obtain predominantly the acrylic acid dimer or predominantly oligomers having a longer chain. The mixture obtained according to this process contains from 1% to 99% by weight of non-polymerized acrylic acid, which can be distilled so as to be recycled into the process after the addition of a polymerization inhibitor. Alternatively, the mixture is used as it is without purification for the preparation of polyacrylic acid derivatives in the adhesive field.

U.S. Pat. No. 4,359,564 describes the synthesis of acrylic acid oligomers used as comonomers in solution or emulsion polymerizations. According to one embodiment, the synthesis is carried out starting from acrylic acid in the presence of a crown ether and of a low content of potassium acrylate, and in the presence of hydroquinone methyl ether (HQME, polymerization inhibitor), at a temperature of 80° C. for 300 hours. The average degree of oligomerization of the acrylic acid is about 3. According to another embodiment, the acrylic acid is heated at a higher temperature, of 120-125° C., for a shorter period of time, in contact with a strongly acidic ion exchange resin in the presence of a mixture of two polymerization inhibitors. Depending on the reaction time, the average degree of oligomerization of the acrylic acid is 1, 4 or 2.

According to the prior art processes, the synthesis of acrylic acid oligomers is always carried out in the presence of a polymerization inhibitor at a relatively high content, and results in a highly stabilized final product, which can be prejudicial for the use of this product as a co-monomer in polymerization processes.

In addition, depending on the envisaged applications of the (co)polymers obtained from acrylic acid oligomers, it may be advantageous to have available acrylic acid oligomers which exhibit a controlled distribution of the oligomeric species.

It remains therefore a need to produce acrylic acid oligomers in high concentration, comprising both a low stabilizer content, and a controlled distribution of the oligomeric species.

Surprisingly, it has been found that the presence of a low amount of water in combination with an acid or basic catalyst makes it possible to reduce the consumption of polymerization inhibitor during the reaction while at the same time controlling the concentration and the distribution of the oligomeric species during the heating of the acrylic acid at a moderate temperature.

This decrease in consumption of polymerization inhibitor makes it possible to lower and to globally control the inhibitor content during the production of oligomers and to obtain a lower final content of inhibitor in the product, which is advantageous to the use of these oligomers in polymerization processes.

SUMMARY OF THE INVENTION

A subject of the invention is therefore a process for the synthesis of an acrylic acid oligomer represented by formula (I):

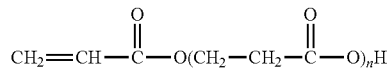

in which n is an integer ranging from 1 to 10, preferably from 1 to 6, characterized in that it comprises heating acrylic acid at a temperature ranging from 50° C. to 200° C. in the presence of a catalyst, of water and of at least one polymerization inhibitor.

Formula (I) in which n=0 represents acrylic acid, the precursor for preparing the acrylic acid oligomer.

According to one embodiment, n is an integer ranging from 1 to 10, preferably from 1 to 6, for example from 1 to 4.

In the remainder of the text, the expressions "between . . . and . . . ", "ranging from . . . to . . . " and "varying from . . . to . . . " are equivalent and are intended to signify that the limits are included, unless otherwise mentioned.

The expressions "oligomer species", "oligomers" or "oligomeric species" are equivalent, and exclude acrylic acid polymers with a degree of polymerization greater than 10.

The term "oligomerization" is intended to mean a polymerization by Michael addition resulting in oligomeric species.

According to the invention, the acrylic acid oligomer is in the form of a liquid at ambient temperature, comprising a mixture of acidic species of formula (I) of various chain lengths depending on the value of n, such as the acrylic acid dimer (also called 3-(acryloyloxy)propionic acid, n=1), the acrylic acid trimer (n=2), the acrylic acid tetramer (n=3), etc. The liquid may contain unreacted acrylic acid (n=0), and water. It is at least partially soluble in water.

For simplification, in the remainder of the disclosure, the acrylic acid dimer will be referred to as di-AA, the acrylic acid trimer will be referred to as tri-AA and the oligomer species for which n>2 in formula (I) will be referred to as oligo-AA.

The process according to the invention may also comprise a purification step comprising at least one distillation in order to eliminate the water and/or the residual acrylic acid.

The acrylic acid oligomer represented by formula (I) that can be obtained according to the process according to the invention comprises from 10 to 2000 ppm of polymerization inhibitor, preferably from 50 to 2000 ppm, in particular from 100 to 1000 ppm, even more particularly from 200 to 500 ppm of polymerization inhibitor.

The acrylic acid oligomer of formula (I) that can be obtained according to the process according to the invention is used as a (co)monomer for preparing acrylic polymers.

Another subject of the invention is a process for the synthesis of an acrylic acid oligomer represented by formula (I):

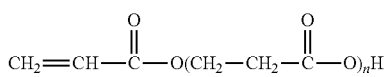

in which n is an integer ranging from 1 to 10, preferably from 1 to 6, characterized in that it comprises the following steps:
a) acrylic acid is heated at a temperature ranging from 50° C. to 200° C. in a reactor comprising a catalyst, in the presence of water, and in the presence of at least one polymerization inhibitor, resulting in a reaction mixture comprising acrylic acid oligomers, acrylic acid, water and polymerization inhibitors;
b) the reaction mixture is subjected to a first distillation which makes it possible to separate a top stream comprising water and acrylic acid, which can be at least partially sent back to the reactor, and at the bottom a stream comprising acrylic acid oligomers, residual acrylic acid and polymerization inhibitors;
c) the bottom stream is subjected to a second distillation which makes it possible to separate a stream comprising essentially acrylic acid and a stream comprising essentially the acrylic acid oligomer of formula (I) and the polymerization inhibitors;
d) the acrylic acid stream is recycled to step a);
e) optionally, the stream comprising the acrylic acid oligomer obtained in step c) is subjected to a film evaporator which makes it possible to separate, on the one hand, a stream consisting essentially of acrylic acid dimers and trimers and, on the other hand, a stream consisting essentially of acrylic acid oligomers corresponding to formula (I) in which n is an integer ranging from 2 to 10, preferably ranging from 3 to 10.

The distillation performed in step b) and in step c) can be carried out by means of a conventional distillation column, or by means of a falling film evaporator.

The stream resulting from step b) can also be subjected to other separation processes, such as crystallization or liquid-liquid extraction.

The present invention makes it possible to overcome the drawbacks of the prior art. It more particularly provides a process for the synthesis of an acrylic acid oligomer making it possible to adjust the composition of the oligomer species present, and comprising a low content of stabilizer (other name for polymerization inhibitor).

This is accomplished by virtue of the presence of water which makes it possible to stabilize the reaction mixture in the presence of a catalyst which may be an acid or basic catalyst, and to reduce the amount of polymerization inhibitor to be used in order to control the oligomerization of the acrylic acid. Since the consumption of polymerization inhibitor is reduced by virtue of the combination of operating conditions used for the thermal reaction of the acrylic acid, it is possible to adjust the amount of polymerization inhibitor to be introduced into the reaction medium to the amount desired in the oligomer produced.

BRIEF DESCRIPTION OF THE FIGURES

FIG. 1 represents diagrammatically one embodiment of the process according to the invention.

DETAILED DESCRIPTION OF THE INVENTION

The invention is now described in greater detail and in a non-limiting manner in the description that follows.

In the process of the invention, acrylic acid is used as starting material which is subjected to a thermal treatment under certain conditions so as to bring about a controlled oligomerization of said acid resulting in a mixture of oligomer species of variable length.

The acrylic acid may be of petrochemical origin or at least partly of renewable origin.

According to one embodiment of the invention, the acrylic acid is of petrochemical origin and derives from a production process using propylene or propane as starting material.

According to one embodiment of the invention, the acrylic acid derives from a process using acetic acid as starting material.

According to one embodiment of the invention, the acrylic acid is of renewable origin and derives from a production process using glycerol or glycerin as starting material.

According to one embodiment of the invention, the acrylic acid is obtained from sugars.

According to one embodiment, the acrylic acid is of renewable origin and it is derived from a process of dehydration of lactic acid or of ammonium lactate to acrylic acid, or from a process of dehydration of 3-hydroxypropionic acid or the ammonium salt thereof to acrylic acid.

The process according to the invention comprises a thermal reaction at a temperature ranging from 50° C. to 200° C., preferably from 80° C. to 140° C., for example between 90° C. and 125° C.

The process is generally carried out under normal pressure or under reduced pressure, the pressure ranging from atmospheric pressure to approximately 50 mbar, or under excess pressure, the pressure possibly ranging up to 20 bar.

The acrylic acid is brought into contact with a catalyst. The catalyst may be an acid or basic catalyst. The catalyst may be homogeneous or heterogeneous.

As homogeneous acid catalyst, use may be made for example of a sulphonic organic acid, such as methanesulphonic acid, para-toluenesulphonic acid, benzenesulphonic acid, dodecylsulphonic acid, xylenesulphonic acid, or mixtures thereof, or sulphuric acid, or polymerizable acrylic compounds such as 2-acrylamido-2-methylpropane sulphonic acid (AMPS) sold by the company Lubrizol.

As heterogeneous acid catalyst, use may be made for example of an ion exchange resin, for example a sulphonated cationic resin, or a strongly acidic zeolite. The catalySt is advantageously a strong cationic resin of styrene/divinylbenzene type comprising sulphonic groups. By way of examples of resins, mention may be made of the Amberlyst A16 resin or the Amberlyst A15 resin sold by the company Dow.

As homogeneous basic catalyst, use may be made for example of sodium hydroxide, potassium hydroxide, carbonates or amino bases.

As heterogeneous basic catalyst, use may be made for example of a strongly basic ion exchange resin, for example an anionic resin. By way of examples of resins, mention may be made of the Amberlyst A28 resin sold by the company Dow.

As catalysts that can be used, mention may also be made of metal catalysts or Lewis acid catalysts, such as iron chloride, aluminium chloride, palladium acetate or palladium hydroxide.

The weight amount of homogeneous catalyst is generally between 0.1% and 20%, preferably between 1% and 10%, relative to the weight of acrylic acid.

The thermal reaction is carried out in the presence of at least one polymerization inhibitor chosen for example from phenothiazine, hydroquinone, hydroquinone monomethyl ether (HQME), hindered phenols such as di-cert-butyl paracresol (BHT) or di-tert-butylcatechol, para-phenylenediamine, TEMPO (2,2,6,6-tetramethyl-1-piperidinyloxy), or TEMPO derivatives, such as 0171-TEMPO, alone or mixtures thereof in any proportion. Preferably, HQME is used as polymerization inhibitor.

The reaction medium contains a small amount of at least one polymerization inhibitor relative to the total weight of acrylic acid used in the process. The weight amount of polymerization inhibitor used is between 10 and 2000 ppm, preferably between 50 and 2000 ppm, in particular between 100 and 1000 ppm, even more particularly between 200 and 500 ppm relative to the weight of acrylic acid.

According to one advantageous embodiment of the present invention, use is made of a combination of a polymerization inhibitor of phenolic type, for example hydroquinone or hydroquinone monomethyl ether, in a content ranging from 10 to 2000 ppm, preferably from 100 to 1000 ppm, with a nitrogenous polymerization inhibitor of TEMPO type or a TEMPO derivative in a content ranging from 1 to 200 ppm, preferably from 10 to 60 ppm.

The thermal acrylic acid oligomerization reaction is carried out with a controlled injection of oxygen-depleted air when the polymerization inhibitors are phenolic compounds.

According to the invention, the reaction medium contains a small amount of water relative to the total weight of acrylic acid used in the process. The amount of water used to prepare the acrylic acid oligomer may represent from 0.01% to 20% by weight, preferably from 0.1% to 5% by weight, in particular from 0.5% to 3% by weight, relative to the weight of acrylic acid.

According to one embodiment of the present invention, a basic catalyst such as sodium hydroxide or potassium hydroxide is used, and the water present in the reaction medium comes from the reaction of the acrylic acid with the catalyst; it is not then necessary to add water to the reaction medium.

The thermal reaction time is generally between 1 and 20 hours.

The thermal reaction can be carried out in a stirred reactor, or in several stirred reactors in cascade, equipped with a jacket, or in a stirred loop reactor containing a fixed bed of catalyst, safety devices being combined with the reactors (rupture disc, injection of an agent for stopping polymerization in the event of the reaction running away, cooling of the reaction mass, pressure control).

The process according to the invention may be carried out batchwise, semi-continuously with gradual introduction of the acrylic acid, or continuously.

The polymerization inhibitors can be introduced separately, or by using an acrylic acid pre-stabilized with the desired amount of inhibitor.

The process according to the invention makes it possible to obtain an acrylic acid oligomer of formula (I) comprising a final content of polymerization inhibitor ranging from 10 to 2000 ppm, preferably from 50 to 2000 ppm, in particular from 100 to 1000 ppm, even more particularly from 200 to 500 ppm, which is entirely compatible with its use as a (co)monomer in radical polymerization processes.

The process according to the invention makes it possible to obtain an acrylic acid oligomer of formula (I), generally as a mixture with free acrylic acid (in the non-polymerized state) in weight proportions that can range from 1/99 to 99/1, preferably from 20/80 to 99/1 (expressed as oligomer/acid weight proportion).

According to one embodiment, the residual acrylic acid content is less than 60% by weight, for example less than 40% or than 20% or than 10% by weight relative to the total weight of the oligomer.

The process according to the invention makes it possible to obtain an acrylic acid oligomer comprising a high content of di-AA dimers and tri-AA trimers, for example greater than 20% by weight, in particular greater than 22% or than 24% by weight relative to the total weight of the oligomer.

The acrylic acid oligomer obtained according to the process according to the invention can be characterized by an average degree of oligomerization.

The average degree of oligomerization is defined by a number average of the oligomer species obtained according to the process of the invention. It can in particular be determined from a measurement of the acid number of the liquid obtained. The acid number (AN in meq of acid per gram) is determined by means of a potentiometric assay.

The average number N of oligomerization is determined by means of the acid number AN according to the formula:

$$N = -1.443 \ln(AN) + 3.7946.$$

The average degree of oligomerization of the acrylic acid oligomer obtained according to the process of the invention is between 0.1 and 10, preferably between 0.1 and 3, for a product essentially consisting of a fraction rich in dimers and trimers, or between 3 and 10 for a product which contains essentially oligomers of formula (I) with n>2.

The process according to the invention also makes it possible to limit the formation of impurities in the acrylic acid oligomer, for example the formation of 3-hydroxypropionic acid (3-HPA). The 3-HPA content is generally less than 1% by weight, for example less than 0.8% by weight, relative to the oligomer formed under the conditions of the process according to the invention.

The acrylic acid oligomerization reaction can be controlled by monitoring the acidity which decreases during the thermal reaction.

According to one embodiment, the process according to the invention also comprises a purification step comprising at least one distillation in order to eliminate the water and/or the residual acrylic acid.

Advantageously, the purification step comprises a first distillation making it possible to separate the water and the acrylic acid, and a film evaporator for separating the dimers and trimers from the oligomers of higher molecular weight.

Advantageously, the acrylic acid and also the water are sent back to the thermal reaction step.

With reference to FIG. 1, which represents a preferred embodiment of the process according to the invention, a reactor R is fed with an acrylic acid stream 1 and a water stream 2. The acrylic acid contains the desired amount of polymerization inhibitor. The reactor comprises a fixed bed of an ion exchange resin, said bed being maintained at a temperature ranging from 50° C. to 200° C. and preferably at atmospheric pressure. The feed flow rates are adjusted so as to have a residence time suitable for the desired conversion for the acrylic acid.

The reaction mixture 3 at the outlet of the reactor is subjected to a distillation in a column C which separates, at the top, a stream 6 comprising the water and acrylic acid, and at the bottom, a stream 5 comprising the acrylic acid oligomers formed in the reactor R, the acrylic acid which is not converted to oligomer and the amount of polymerization inhibitor that was not consumed during the thermal treatment.

The top flow 6 is advantageously partly recycled to the reaction via the stream 10, the other part 11 being sent to a water treatment station.

The stream 5 comprising the acrylic acid oligomer of formula (I) is subjected to a distillation column C1 in order to separate the residual acrylic acid which is advantageously recycled to the reactor via the stream 4.

A final treatment by means of a film evaporator E can be carried out on the oligomer stream 7, from which the residual acrylic acid has been removed, in order to isolate a mixture 9 consisting mainly of acrylic acid dimer and trimer, from all the oligomers present.

According to one embodiment, the acrylic acid oligomer obtained according to the process of the invention is used as it is without a step of separating the residual acrylic acid, as a (co)monomer for producing acrylic polymers.

According to one embodiment, the residual acrylic acid is eliminated before using the acrylic acid oligomer obtained according to the process of the invention as a (co)monomer for producing acrylic polymers.

According to one embodiment, the acrylic acid dimer and trimer mixture obtained according to the process of the invention is used as a (co)monomer for producing acrylic polymers.

The acrylic polymers comprising at least one monomer consisting of an acrylic acid oligomer obtained according to the invention are advantageously used for preparing acrylic dispersants or thickeners, hydrophilic adhesives or acrylic coatings.

The invention is now illustrated by the following examples, which are not intended to limit the scope of the invention, defined by the appended claims.

EXAMPLES

Unless otherwise indicated, the percentages as expressed as weight percentages. The following abbreviations are used:
AA: acrylic acid
di-AA: acrylic acid dimer
tri-AA: acrylic acid trimer
oligo-AA:

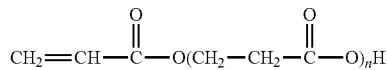

with n>2
HQME: hydroquinone methyl ester
4-OH-T: 4-hydroxy-TEMPO
A16: Amberlyst A16 resin.

The AA, di-AA, tri-AA and HQME contents in the various synthesis tests were determined by HPLC analysis. The HQME contents measured by HPLC have a margin of error of about 2%.

The determination of the AA, di AA and tri-AA contents makes it possible to estimate the oligo-AA content (by difference to 100).

The acid number (AN in meq of acid per gram) is determined by means of a potentiometric assay. The lower the acid number, the higher the concentration of oligomer will be.

The average number N of oligomerization will be determined by means of the acid number AN according to the formula:

$$N = -1.443 \ln(AN) + 3.7946.$$

Example 1 (Comparative): Batchwise Test in the Absence of Resin and of Water

The following were introduced into a perfectly stirred, three-necked reactor equipped with a temperature probe and surmounted by a reflux condenser:
200 g of AA
0% of water
0% of A16 resin
1023 ppm of HQME.
The reaction medium was stirred for eight hours at 97° C. with air bubbling. After 8 h, the reaction medium comprises:
AA: 92.5%
di-AA: 7.06%
tri-AA: 0.2%
final HQME content: 1022 ppm. HQME consumption: 0%
AN=13.46 meq/g
N=0.043.
The di-AA content is less than 10%.
In this test, the HQME consumption is zero.

Example 2 (Comparative): Batchwise Test in the Presence of Resin and in the Absence of Water Example 1 was reproduced in the presence of A16 resin:
200 g of AA
0% of water
20% of A16 resin
1264 ppm of HQME.
After 8 h, the reaction medium comprises:
AA: 83.55%
di-AA: 13.71%
tri-AA: 1.31%
Final HQME content: 524 ppm. HQME consumption: 58.5%
AN=12.49 meq/g
N=0.151.
The presence of the resin makes it possible to considerably increase the acrylic acid dimer and trimer yield, which doubled compared with example 1. The average oligomerization number tripled compared with example 1. However, the resin generates a very significant consumption of HQME stabilizer (>50%).

Example 3 (According to the Invention): Batchwise Test in the Presence of Resin and of Water Example 1 was reproduced with the addition of water and in the presence of A16 resin:

200 g of AA
1% of water
20% of A16 resin
661 ppm of HQME.

After 8 h, the reaction medium comprises:
AA: 80.06%
di-AA: 12.89%
tri-AA: 1.47%
Final HQME content: 581 ppm. HQME consumption:
AN=12.21 meq/g
N=0.184.

The total dimer and trimer yield is similar to example 2. However, the addition of 1% of water makes it possible to very considerably limit the HQME consumption (12% compared with 58.5%).

Example 4 (According to the Invention): Batchwise Test in the Presence of Resin and of Water, Effect of Temperature Example 3 was reproduced at 107° C.:
200 g of AA
1% of water
20% of A16 resin
642 ppm of HQME.

After 8 h, the reaction medium comprises:
AA: 59.41%
di-AA: 22.41%
tri-AA: 4.94%
Final HQME content: 545 ppm. HQME consumption: 15%
AN=10.69 meq/g
−N=0.376.

The temperature increase of 10° C. made it possible to increase the dimer+trimer yield very considerably. The acid number decreased and the average oligomerization number increased. The presence of 1% of water made it possible once again to limit the HQME consumption.

Example 5 (Comparative): According to U.S. Pat. No. 4,359,564

The following were introduced into a perfectly stirred, three-necked reactor equipped with a temperature probe and surmounted by a reflux condenser:
100 g of AA
0% of water
20% of A15 resin
1342 ppm of HQME.

The reaction medium was stirred for 9.5 hours at 125° C. with air bubbling.

After 9.5 h, the reaction medium comprises:
AA: 24.06%
di-AA: 19.22%
tri-AA: 10%
Final HQME content: 532 ppm. HQME consumption: 60%
AN=7.35 meq/g
N=0.915.

The AA consumption is high, the average oligomerization number is equal to 0.915 demonstrating the presence of oligomeric species, and the dimer content is high. However, the HQME consumption is still very high (60%).

Example 6 (According to the Invention)

Example 5 was reproduced with:
100 g of AA
5% of water
20% of A15 resin
1484 ppm of HQME.

The reaction medium was stirred for 9.5 hours at 125° C. with air bubbling.

After 9.5 h, the reaction medium comprises:
AA: 22.04%
di-AA: 17.3%
tri-AA: 8.51%
Final HQME content: 1048 ppm. HQME consumption: 30%
AN=7.08 inapt
N=0.971.

The results in terms of oligomerization number, di-AA and tri-AA are similar. The addition of water was beneficial for the consumption of HQME stabilizer.

Example 7 (According to the Invention): Test in the Presence of a Basic Catalyst and in the Presence of Water The following were introduced into a perfectly stirred, three-necked reactor equipped with a temperature probe and surmounted by a reflux condenser:
100 g of AA
1% of water
1% of sodium hydroxide
589 ppm of HQME.

The reaction medium was stirred for 8 hours at 97° C. with air bubbling.

After 8 h, the reaction medium comprises:
AA: 65.24%
di-AA: 22.46%
tri-AA: 2.98%
Final HQME content: 594 ppm. HQME consumption: 0%
AN=10.96 meq/g
N=0.339.

Compared with examples 1, 2 and 3 at the same temperature, the dimer and trimer contents are higher; the basic catalyst makes it possible to improve the acrylic acid oligomerization reaction. The presence of water also makes it possible to avoid any HOME consumption.

Example 8 (According to the Invention): Continuous Test

A reaction mixture consisting of AA, of water and of HQME continuously feeds a glass reactor with a volume of 160 ml by means of a membrane pump. This glass reactor consists of a preheater, connected to a glass column containing a fixed bed of catalyst (A16 resin), heated by means of a jacketed oil bath, surmounted by a reflux condenser and connected to a condenser. The assembly is lagged. Continuous air bubbling is performed.

The feed contains: AA, 12000 ppm of water, and 961 ppm of HQME. The feed flow rate is 60 ml/h.

After a residence time of 2.6 hours at 107° C., the composition of the medium is the following:
di-AA: 22.17%
tri-AA: 5.46%
Final HQME content: 699 ppm. HQME consumption: 27.2%
AN=10.48 meq/g
N=0.405.

On a fixed resin bed, at the same temperature as example 3, the average oligomerization number is higher even though the residence time has been divided by four. The presence of 12000 ppm of water makes it possible to limit the HQME consumption.

Example 9 (According to the Invention):
Continuous Test

Example 8 was reproduced with the following feed: AA, 6000 ppm of water, 723 ppm of HQME.
After a residence time of 2.4 h at 102° C., the composition of the medium is the following:
di-AA: 23.12%
tri-AA: 6.23%
Final HQME content: 469 ppm. HQME consumption: 35%
N=10.23 meg/g
N=0.439.

The decrease in the water content at the start compared with example 8 accelerates the HQME consumption. This proves once more the beneficial advantage of water with the resin for limiting the HQME consumption.

The invention claimed is:

1. A process for the synthesis of an acrylic acid oligomer represented by the formula (I):

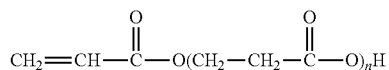

in which n is an integer ranging from 1 to 10,
wherein said process comprises the step of heating acrylic acid at a temperature ranging from 50° C. to 200° C. in the presence of a catalyst, water and at least one polymerization inhibitor.

2. The process according to claim 1, wherein the acrylic acid is of petrochemical origin.

3. The process according to claim 1, wherein the acrylic acid is at least partly of renewable origin.

4. The process according to claim 1 wherein the catalyst is a homogeneous acid catalyst or a heterogeneous acid catalyst.

5. The process according to claim 1 wherein the catalyst is a homogeneous basic catalyst or a heterogeneous basic catalyst.

6. The process according to claim 5, wherein the basic catalyst is sodium hydroxide or potassium hydroxide, and the water present in the reaction medium comes from the reaction of the acrylic acid with the catalyst, without the addition of water to the reaction medium.

7. The process according to claim 1 wherein the weight amount of water used represents from 0.01% to 20% relative to the weight of acrylic acid.

8. The process according to claim 1 wherein the weight amount of polymerization inhibitor used is between 10 and 2000 ppm relative to the weight of acrylic acid.

9. The process according to claim 1 wherein the polymerization inhibitor is chosen from the group consisting of phenothiazine, hydroquinone, hydroquinone monomethyl ether, hindered phenols, TEMPO (2,2,6,6-tetramethyl-1-piperidinyloxy), and TEMPO derivatives, alone or mixtures thereof in any proportions.

10. The process according to claim 1 comprising a purification step comprising at least one distillation to eliminate water and/or residual acrylic acid.

11. A process for the synthesis of an acrylic acid oligomer represented by formula (I):

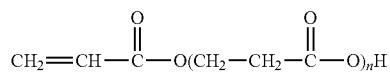

in which n is an integer ranging from 1 to 10,
the process comprising the following steps:
a) heating acrylic acid at a temperature ranging from 50° C. to 200° C. in a reactor comprising a catalyst, in the presence of water and at least one polymerization inhibitor, resulting in a reaction mixture comprising acrylic acid oligomers, acrylic acid, water and polymerization inhibitors;
b) subjecting the reaction mixture to a first distillation to enable separation of a top stream comprising water and acrylic acid, which is at least partially sent back to the reactor, and at the bottom a stream comprising acrylic acid oligomers, residual acrylic acid and polymerization inhibitors;
c) subjecting the bottom stream to a second distillation to enable separation of a stream consisting essentially of acrylic acid and a stream consisting essentially of the acrylic acid oligomer of formula (I) and the polymerization inhibitors;
d) recycling the acrylic acid stream to step a);
e) optionally, subjecting the stream comprising the acrylic acid oligomer obtained in step c) to a film evaporator to enable the separation of, on the one hand, a stream consisting essentially of acrylic acid dimers and trimers and, on the other hand, a stream consisting essentially of acrylic acid oligomers, corresponding to formula (I) in which n is an integer ranging from 2 to 10.

* * * * *